United States Patent [19]  [11] 4,002,737
Borris  [45] Jan. 11, 1977

[54] PREVENTION AND/OR TREATMENT OF POISON IVY DERMATITIS

[75] Inventor: David P. Borris, Oxford, Miss.

[73] Assignee: Research Corporation, New York, N.Y.

[22] Filed: Oct. 15, 1975

[21] Appl. No.: 622,520

[52] U.S. Cl. ................................................. 424/94
[51] Int. Cl.² ...................................... A61K 37/48
[58] Field of Search .................................... 424/94

[56] References Cited
OTHER PUBLICATIONS

Chem. Abst., 8th Collective Index, vol. 66–75 (1967–1971) p. 22230s.

Primary Examiner—Sam Rosen
Attorney, Agent, or Firm—Cooper, Dunham, Clark, Griffin & Moran

[57] ABSTRACT

The enzymes catechol 1,2-oxygenase and catechol 2,3-oxygenase and mixtures thereof are useful in the prevention and/or treatment of poison ivy dermatitis.

10 Claims, No Drawings

PREVENTION AND/OR TREATMENT OF POISON IVY DERMATITIS

This invention relates to the prevention and/or treatment of poison ivy dermatitis due to contact of the skin with the toxic component of poison ivy. This invention in its broadest aspects is not only directed to the prevention and/or treatment of poison ivy dermatitis but also to the prevention and/or treatment of dermatitis brought upon by the contact of the skin with the active toxin of poison oak and poison sumac.

the active toxin in poison ivy, poison oak and poison sumac has long been known to belong to a group of organic compounds called urushiol. Urushiol has been identified as comprising a number of compounds. Four have been identified and each of the compounds is a 1,2-dihydroxy benzene (catechol) with a 15-carbon atom side chain in the 3 position. The only difference among the compounds of urushiol is the degree of unsaturation in the alkyl side chain, see C. R. Dawson, *Record Chem. Prgr.*, 15, 39 (1954) and B. Loev & C. R. Dawson, *J. Am. Chem. Soc.*, 78 (6), 1180 (1956). These four compounds have been identified as 3-pentadecylcatechol, 3-(8-pentadecenyl)-catechol, 3-(8,11-pentadecadienyl)-catechol and 3-(8,11,14-pentadecatrienyl)-catechol.

Upon contact of the skin with the active toxin, urushiol, of poison ivy, poison oak and poison sumac, skin irritation, inflammation and blistering usually results. Various therapeutic agents have been proposed for the treatment of contact dermatitis due to poison ivy, poison oak and poison sumac but no agent has been found to be effective to prevent dermatitis due to contact with urushiol.

Zirconium oxide has been proposed and used therapeutically but this material has not been found to be completely effective and sometimes causes allergenic hypersensitivity. Oxidizing agents, such as potassium permanganate and hydrogen peroxide, have been proposed but are limited due to their slow inactivation of urushiol because of their own labile character and non-selective oxidation. Tyrosinase, one of the phenol oxidases, has been suggested but the resulting reaction product has been shown to have toxicity. The medical literature is rich with studies of poison ivy dermatitis and the treatment thereof, see *AMA Archives of Dermatology*, Vol. 77, 149–180 (1958), *J.A.M.A.*, Dec. 7, 1964, Vol. 190, pages 162–164, *Archives of Dermatology*, 92, 188 (1965), *Immunochemistry*, Vol. 3, pages 479–485, published by Pergamon Press (1966), *J. Amer. Pharm. Assoc.*, Vol. NS7, No. 2, pages 65–67 (1967) and *Journal of Medicinal Chemistry*, Vol. 14, No. 8, pages 729–732 (1971). The disclosures of the above-identified publications are herein incorporated and made part of this disclosure.

For the most part, the materials and techniques and agents suggested and proposed heretofore for the prevention and/or treatment of poison ivy dermatitis and the like have not been completely satisfactory.

It is an object of this invention to provide materials useful for the prevention and/or treatment of contact dermatitis from poison ivy, poison oak, poison sumac and the like.

It is another object of this invention to provide a technique and method of treatment for the prevention and/or treatment of contact dermatitis from poison ivy, poison oak, poison sumac and the like.

How these and other objects of this invention are achieved will become apparent in the light of the accompanying disclosure. In at least one embodiment of the practice of this invention at least one of the foregoing objects will be achieved.

It has been discovered that the enzymes catechol 1,2-oxygenase and catechol 2,3-oxygenase and mixtures thereof are useful for the detoxification of the contact toxin or toxic component of poison ivy, poison oak, poison sumac and the like, viz., urushiol, particularly the compounds thereof. Specifically, it has been discovered that urushiol is detoxified by the enzyme catechol 1,2-oxygenase to its corresponding alkylated derivative of cis, cis-muconic acid which is water soluble and non-toxic. The detoxification of urushiol by catechol 1,2-oxygenase is illustrated by the reaction [A]:

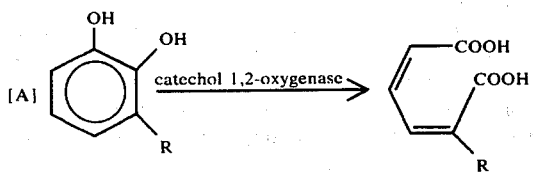

wherein R = saturated, mono, di and tri-unsaturated pentadecyl derivatives

It has also been discovered that urushiol and the components thereof are detoxified by the enzyme catechol 2,3-oxygenase with the production of the corresponding water soluble and non-toxic alkylated derivative of alphahydroxy muconic semialdehyde. The detoxification of urushiol by the enzyme catechol 2,3-oxygenase is illustrated by the reaction [B]:

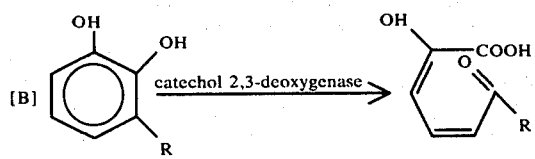

wherein R = saturated, mono, di and tri-unsaturated pentadecyl derivatives

The enzymes catechol 1,2-oxygenase, catechol 2,3-oxygenase and mixtures thereof provide a highly selective means for rapidly oxidizing and detoxifying the toxin (urushiol) of poison ivy, poison oak and poison sumac and the like.

In the practices of this invention it is preferred to employ the enzyme catechol 1,2-oxygenase because of its stability.

In the embodiment of this invention directed to the prevention of contact dermatitis due to contact with urushiol, the enzyme catechol 1,2-oxygenase or catechol 2,3-oxygenase or mixtures thereof would be applied to the skin surface which might come in contact with urushiol, either directly or indirectly, i.e. either by direct contact with poison ivy, poison oak or poison sumac and the like, or indirectly through contact with clothing or an object which had previously come into contact with poison ivy, poison oak and poison sumac and carries the toxin on its surface. With the application to the skin of one or both of the above-identified enzymes, any subsequent contact of the skin with the toxin urushiol should result in the neutralization of the toxin without giving rise to dermatitis. By this embodiment of the invention there is provided for the first time an effective technique for the prevention of contact dermatitis due to contact of the skin with poison ivy, poison oak, poison sumac and the like.

In another embodiment of the practice of this invention for the treatment of contact dermatitis due to contact of the skin with poison ivy, poison oak, poison sumac and the like, the skin surface which experienced contact with the toxin (urushiol) of the aforementioned plants with resulting indication of dermatitis derived from this contact and the surrounding skin surfaces and those skin surfaces which might come in contact with the toxin derived from the aforementioned contact, such as by scratching or rubbing, has applied thereto the enzyme catechol 1,2-oxygenase or catechol 2,3-oxygenase or mixtures thereof. Upon contact of the enzyme to the skin containing the toxin, the toxin would be rapidly detoxified. Both enzymes effectively convert the toxin to a water soluble product which can then be readily cleared and removed from the skin by washing, such as by washing with soapy water.

In the practice of this invention for the prevention and/or treatment of contact dermatitis due to contact of the skin with the toxin (urushiol) of poison ivy, poison oak or poison sumac, the enzyme catechol 1,2-oxygenase or catechol 2,3-oxygenase or mixtures thereof is applied to the skin in a suitable carrier. The carrier containing the enzyme or the enzyme-carrier composition desirably provides not only a support for the enzyme, usually present in a minor amount, such as in the range 0.01–2.5% by weight of the enzyme-carrier composition, but also provides a non-irritating, dermatologically physiologically acceptable vehicle for application of the enzyme to the skin. Suitable carriers for the enzyme include both liquid-form carriers, cream-like carriers and solid-form carriers or compositions, such as inert, finely divided, powder, inorganic or organic, e.g. talc, silica or other inert powdery material. Solutions, dispersions or emulsions containing the enzyme, aqueous or non-aqueous, preferably water-washable or water-dispersible cream-like emulsions or dispersions, are particularly useful. The enzyme might also be incorporated in compositions suitable for dispensing in aerosol form.

The enzyme, as indicated hereinabove, might be conveniently adsorbed on or incorporated in solid particle-form material, such as talc, and the enzyme-talc composition applied to the skin by dusting or powdering. Such compositions might be useful in the prevention of dermatitis by applying these compositions to the skin before risking the skin to contact with the toxin. The enzyme might also be immobilized on a suitable substrate rather than by mere physical adsorption thereon and the resulting immobilized enzyme applied directly to the skin. The substrate containing the immobilized enzyme might be in finely divided form suitable for dusting or in tape or bandage form whereby the surface of the tape or bandage containing the immobilized enzyme can be placed directly upon the skin surface exposed to contact with the toxin.

Liquid or cream-like compositions, including aqueous, non-aqueous (hydrophobic) solutions or dispersions and water-dispersible or water-washable oil-in-water emulsions and water-in-oil emulsion compositions are particularly useful in the practices of this invention when employed as vehicles or carriers for the enzyme for direct application to the skin.

As indicated hereinabove, each of the enzyme-containing compositions contain the enzyme either as free enzyme or adsorbed or immobilized or dissolved or dispersed therein. Suitable enzyme compositions of this invention would contain a minor but effective amount of the enzyme, such as from about 0.001% up to about 5% by weight, more or less. A particularly preferred carrier for the enzyme in accordance with this invention are the low molecular weight, normally liquid aliphatic organic compounds, such as acetone and the $C_1$–$C_3$ alkanols, e.g. ethanol, such as an aqueous solution of ethanol containing about 2–20% $C_2H_5OH$, usually about 10%. It has been found that low concentrations of the enzyme, e.g. catechol 2,3-oxygenase which is unstable and easily inactivated in the presence of air, in organic solvents, such as acetone and alcohol, yield an enzyme-containing composition or solution wherein the enzyme is almost completely protected from inactivation by air.

In the make-up of the enzyme compositions it has been observed that crude enzyme, particularly crude catechol 1,2-oxygenase, is stable for long periods of time when maintained at a temperature below room temperature, such as about 4° C., and at a pH of about 7.0–8.0. The purified enzyme (catechol 1,2-oxygenase) is less stable and loses a minor amount, about 15%, of its activity during storage for about 4 days at 4° C. The enzyme, such as the enzyme catechol 1,2-oxygenase, is readily prepared from a microbiological source, see *Biochemica et Biophysica Acta*, 147, 189–199 (1967), the article entitled "Purification and Properties of Pyrocatechase from *Pseudomonas fluorescens* (ATCC 11250)" and see also the *Journal of Biological Chemistry*, Vol. 242, No. 14, pages 3270–3278 (1967) which discloses the purification of pyrocatechase from *Pseudomonas avila*. The disclosures of the above-identified publications are also herein incorporated and made part of this disclosure. The enzyme pyrocatechase or catechol 1,2-oxygenase may also be derived from *Brevibacterium fuscum*. Like pyrocatechase, the enzyme metapyrocatechase or catechol 2,3-oxygenase is an inducible enzyme and is obtainable from *Pseudomonas avila* and other microbiological species.

The enzyme catechol 1,2-oxygenase is obtained by growing *Pseudomonas fluorescens* ATCC 11250 in a yeast extract medium containing benzoic acid as the principal carbon source to induce the formation of the enzyme, e.g. catechol 1,2-oxygenase. The enzyme is then isolated by $(NH_4)_2SO_4$ fractionation, DEAE cellulose chromatography and polyacylamide gel electrophoresis. The resulting purified enzyme was found to be active in 10% aqueous ethanol and readily cleaved purified urushiol isolated from poison ivy, poison oak and poison sumac, as indicated in reaction [A] hereinabove.

The effectiveness of the enzymes of this invention, catechol 1,2-oxygenase and catechol 2,3-oxygenase, for the neutralization or detoxification of the compounds of urushiol is indicated by tests wherein 3-alkyl catechols were employed as substrates with catechol 1,2-oxygenase. The 3-alkyl catechols, 3-penta, 3-nonyl and 3-pentadecylcatechols, were synthesized by a procedure similar to that of C. R. Dawson et al. *J. Med. Chem.*, 14, 729 (1971). In these tests the catechol 1,2-oxygenase was derived and purified from *Pseudomonas fluorescens* ATCC 11250. These tests show that the enzyme catechol 1,2-oxygenase was effective in converting the above-identified alkyl catechols to the corresponding alkylated derivatives of cis, cis-muconic acid, which are dermatologically non-toxic, thereby effectively demonstrating the applicability of the enzymes employed in the practice of this invention for the prevention and/or treatment of contact dermatitis from poison ivy, poison oak and poison sumac.

Other tests were carried out on a human wherein patches of the skin had applied thereto solutions of varying concentrations of 3-pentadecylcatechol. In each instance toxic reactions proportional to the concentration of the applied 3-pentadecylcatechol solution were observed. In another test 3-pentadecylcatechol was incubated with one of the enzymes in accordance with this invention, vis. catechol 1,2-oxygenase, and the resulting product was then applied to the skin. No toxic reaction was observed. In another test the enzyme itself, e.g. catechol 1,2-oxygenase, was applied directly to the skin and no toxic reaction was observed. In an additional test a portion of the skin had applied thereto a solution of 3-pentadecylcatechol, a compound or component of urushiol. The thus-treated skin was then exposed to an ethanolic solution of the enzyme catechol 1,2-oxygenase. No toxic reaction was observed but 2 days subsequent to the treatment of the skin with the enzyme solution, a feeble toxic reaction was observed. This indicated that in the first instance not sufficient enzyme had been applied to the skin relative to the amount of the applied 3-pentadecylcatechol.

In the practices of this invention for the treatment of contact dermatitis due to contact with the toxin of such plants as poison ivy, poison oak and poison sumac, multiple applications of the enzyme may be employed as well as a single application. Multiple applications may be employed on the affected area evidencing dermatitis over a period of 1 to 4 days, such as 1 to 4 applications per day.

As will be apparent to those skilled in the art in the light of the foregoing disclosure, many modifications, alterations and substitutions are possible in the practice of this invention without departing from the spirit or scope thereof.

I claim:
1. A method of treating or preventing poison ivy dermatitis which comprises applying to the skin surface susceptible to or evidencing poison ivy dermatitis an effective amount of enzyme selected from the group consisting of catechol 1,2-oxygenase and catechol 2,3-oxygenase.
2. A method in accordance with claim 1 wherein said enzyme is catechol 1,2-oxygenase.
3. A method in accordance with claim 1 wherein said enzyme is catechol 2,3-oxygenase.
4. A method in accordance with claim 1 wherein said enzyme is a mixture of catechol 1,2-oxygenase and catechol 2,3-oxygenase.
5. A method in accordance with claim 1 wherein said enzyme is applied in a dermatologically physiologically acceptable carrier at a concentration in the range 0.001–5% by weight.
6. A method in accordance with claim 1 wherein said enzyme is applied in an alcoholic solution thereof.
7. A method in accordance with claim 6 wherein said alcoholic solution is an ethanolic solution.
8. A method in accordance with claim 1 wherein said enzyme is adsorbed on particulate matter.
9. A method in accordance with claim 1 wherein said enzyme is applied in immobilized form on a dermatologically physiologically acceptable substrate.
10. A method in accordance with claim 1 wherein said enzyme is encapsulated within a dermatologically physiologically acceptable encapsulating agent, said agent being capable of being ruptured or being broken to release said enzyme upon frictional contact when applied with rubbing to the skin.

* * * * *